US006996480B2

(12) United States Patent
Giurgiutiu et al.

(10) Patent No.: US 6,996,480 B2
(45) Date of Patent: Feb. 7, 2006

(54) STRUCTURAL HEALTH MONITORING SYSTEM UTILIZING GUIDED LAMB WAVES EMBEDDED ULTRASONIC STRUCTURAL RADAR

(75) Inventors: Victor Giurgiutiu, Columbia, SC (US); Jingjing Bao, Columbia, SC (US); Andrei N. Zagrai, Jersey City, NJ (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 10/462,583

(22) Filed: Jun. 16, 2003

(65) Prior Publication Data

US 2005/0228597 A1    Oct. 13, 2005

Related U.S. Application Data

(60) Provisional application No. 60/389,063, filed on Jun. 14, 2002, provisional application No. 60/389,065, filed on Jun. 14, 2002.

(51) Int. Cl.
*G01B 5/28* (2006.01)
(52) U.S. Cl. .............................. 702/35; 702/36; 702/39; 702/159
(58) Field of Classification Search ................. 702/35, 702/36, 39, 159; 367/99, 101, 102; 73/570, 73/596, 627, 632, 628, 618, 620, 625, 626, 73/633, 640, 641, 645–648
See application file for complete search history.

(56) References Cited

U.S. PATENT DOCUMENTS

| | | | |
|---|---|---|---|
| 3,675,472 A * | 7/1972 | Kay et al. ..................... 73/602 |
| 3,713,127 A | 1/1973 | Keledy et al. ............... 340/540 |
| 4,497,210 A * | 2/1985 | Uchida et al. ................ 73/602 |
| 4,821,575 A | 4/1989 | Fujikake et al. .............. 73/626 |
| 4,995,260 A | 2/1991 | Deason et al. ................ 73/632 |
| 5,129,399 A * | 7/1992 | Hirama ......................... 600/447 |
| 5,167,157 A | 12/1992 | Wertz et al. .................. 73/627 |
| 5,309,765 A * | 5/1994 | Horigome et al. ............ 73/602 |
| 5,581,517 A * | 12/1996 | Gee et al. .................... 367/138 |
| 5,814,729 A | 9/1998 | Wu et al. ...................... 73/588 |
| 6,006,163 A | 12/1999 | Lichtenwainer et al. ...... 702/36 |

OTHER PUBLICATIONS

International Search Report issued in the co-pending PCT application, dated Dec. 31, 2003.
Heydar T. Shandiz et al., "A New SAFT Method in Ultrasonic Imaging at Very Low Frequency by Using Pulse Echo Method," Nov. 1999.
Emmanuel Moulin et al., "Piezoelectric Transducer Embedded in a Composite Plate: Application to Lamb Wave Generation," *Journal of Applied Physics* 82 (5), Sep. 1, 1997.
International Application Published Under the Patent Cooperation Treaty (PCT) No. WO 02/062206 A3 entitled "In-Situ Structural Health Monitoring, Diagnostics and Prognostics System Utilizing Thin Piezoelectric Sensors," publication date Aug. 15, 2002.
Shankar Sundararaman et al., "Structural Damage Identification in Homogeneous and Heterogeneous Structures Using Beamforming," Oct. 2002.

* cited by examiner

*Primary Examiner*—Michael Nghiem
*Assistant Examiner*—Stephen J. Cherry
(74) *Attorney, Agent, or Firm*—Nelson Mullins Riley & Scarborough LLP (57) ABSTRACT

A method and device for performing ultrasonic damage detection in a thin-wall structure using an array of embedded Piezoelectric Wafer Active Sensors (PWAS) for the transmission and reception of guided waves and a signal processing methodology based on the beamforming process. The beamforming signal processing has been adapted to the specifics of guided elastic waves traveling in thin-wall structures.

27 Claims, 9 Drawing Sheets

| | FIRING PATTERN (SYMBOLS DESIGNATED THE TRANSMITTERS THAT ARE ACTIVATED) | | | | | SYNTHETIC BEAMFORMING RESPONSE |
|---|---|---|---|---|---|---|
| | $T_0$ | $T_1$ | $T_2$ | | $T_{M-1}$ | |
| $R_0$ | $P_{0,0}(t)$ | $P_{0,1}(t)$ | $P_{0,2}(t)$ | ... | $P_{0,M}(t)$ | $W_0(t)$ |
| $R_1$ | $P_{1,0}(t)$ | $P_{1,1}(t)$ | $P_{1,2}(t)$ | ... | $P_{1,M}(t)$ | $W_1(t)$ |
| $R_2$ | $P_{2,0}(t)$ | $P_{2,1}(t)$ | $P_{2,2}(t)$ | ... | $P_{2,M}(t)$ | $W_2(t)$ |
| ... | ... | ... | ... | ... | ... | ... |
| $R_{M-1}$ | $P_{M-1,0}(t)$ | $P_{M-1,1}(t)$ | $P_{M-1,2}(t)$ | ... | $P_{M-1,M-1}(t)$ | $W_{M-1}(t)$ |

RECEIVERS

*FIG. 13*

STRUCTURAL HEALTH MONITORING SYSTEM UTILIZING GUIDED LAMB WAVES EMBEDDED ULTRASONIC STRUCTURAL RADAR

PRIORITY CLAIM

This application claims the benefit of provisional application Ser. No. 60/389,063, filed Jun. 14, 2002, and provisional application Ser. No. 60/389,065, filed Jun. 14, 2002, which are relied upon and incorporated herein by reference.

BACKGROUND OF THE INVENTION

It has been recognized that there is a need to monitor the structural health of various types of vehicles, machines and other types of equipment. To name a few examples, structural health monitoring is desirable in aircraft, critical pressure vessels used in the energy generating industry, oil tanks and pipelines, and the like.

A variety of techniques have been utilized to perform nondestructive evaluation of structures. For example, ultrasonic transducers have been used in portable devices placed in communication with the structure of interest. The crystals propagate ultrasonic waves into the material, which are then detected. The detected signals can be electronically processed to indicate anomalies.

An embedded nondestructive evaluation system for structures is described in U.S. Pat. No. 6,006,163 to Lichtenwalner. This patent describes an active damage interrogation system having an array of piezoelectric transducers attached to or embedded within a structure for both actuation and sensing. After interrogation, the transducer signals are digitized and the transfer function of an actuator/sensor pair is computed. The computed transfer function is compared against a baseline transfer function for the respective pair. The transducers are actuated by broadband excitation over a frequency range of 0 to 100 kHz.

SUMMARY OF THE INVENTION

The present invention addresses the foregoing disadvantages and others of prior art constructions and methods. Accordingly, it is an object of the present invention to provide an improved structural health monitoring system using an embedded sensor array.

It is a further object of the present invention to provide a structural health monitoring system that locates defects over large areas of thin-wall structures using guided ultrasonic waves.

It is another object of the present invention to provide an ultrasonic structural health monitoring system that utilizes beam forming techniques.

It is a further object of the present invention to realize the beamforming pulse-echo technique with minimal instrumentation and least installed power.

Some of these objects are achieved by a system operative to detect a damage feature in a thin wall structure. The system comprises a plurality of piezoelectric sensors embedded on the structure in a predetermined-pattern. A generator is operative to impress a pulse having a predetermined carrier frequency upon at least one of the sensors to produce ultrasonic waves over certain Lamb modes and wavelengths in the thin-wall structure.

The system further includes a signal processor operative to process received signals at the sensors resulting from an echo from the damage feature. The processor implements a synthetic beamforming methodology for determining an angular position of the damage feature relative to the array. In addition, the processor calculates a distance to the damage feature.

Other aspects of the invention are achieved by a system operative to detect a damage feature in a thin wall structure. The system comprises a plurality of piezoelectric sensors embedded on the structure in a linear pattern. A generator is operative to impress a pulse having a predetermined carrier frequency upon the sensors so as to produce ultrasonic-waves in the structure at a predetermined azimuth.

The system further includes a signal processor operative to process the signals received at all the sensors resulting from an echo from the damage feature. The processor further calculates a distance to the damage feature.

A distinctive feature in certain embodiments of the invention is the provision of an operative mode in which very little instrumentation and minimal power are required to implement the phased-array principle. In this "lightweight" mode, excitation is implemented on only one of the array elements at a time and a round-robin procedure is applied to measure a set of primitive signals that are stored in digital format and processed in virtual time after the fact. The number of primitives is $M^2$, where M is the number of elements in the array. This feature is specific to structural health monitoring implementations which allows for extensive signal processing over time. This feature permits inexpensive and lightweight implementation of the phased-array principle.

Other objects, features and aspects of the present invention are provided by various combinations and subcombinations of the disclosed elements, as well as methods of utilizing same, which are discussed in greater detail below.

BRIEF DESCRIPTION OF THE DRAWINGS

A full and enabling disclosure of the present invention, including the best mode thereof directed to one of ordinary skill in the art, is set forth in the present specification, which makes reference to the appended drawings, in which.

DETAILED DESCRIPTION OF PREFERRED EMBODIMENTS

Reference will now be made in detail to the presently preferred embodiments of the invention, one or more examples of which are illustrated in the accompanying drawings. It is to be understood by one of ordinary skill in the art that the present discussion is a description of exemplary embodiments only, and is not intended as limiting the broader aspects of the present invention. It fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variation as come within the scope of the appended claims and their equivalents.

Figure 1:
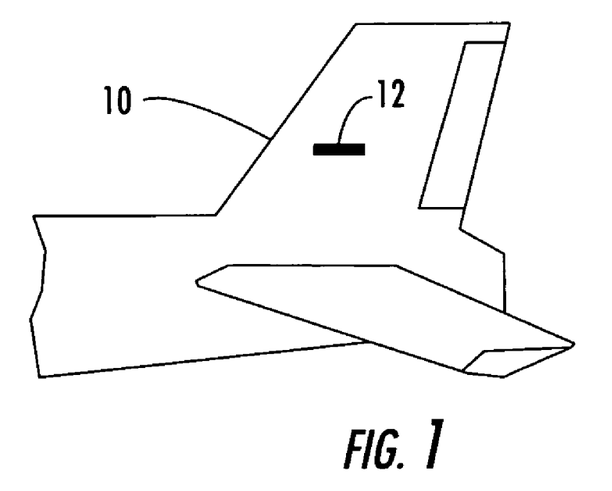
FIG. 1 is a representation of a piezoelectric wafer active sensor (PWAS) array mounted on the tail section of an aircraft to illustrate one application where principles of the present invention can be utilized.

Generally, the present invention relates to embedding relatively small transducers on a thin-wall structure in order to monitor the structure's structural health. For example, FIG. 1 illustrates an aircraft tail section in which a transducer array 12 has been embedded. As will be described more fully below, array 12 preferably comprises a plurality of piezoelectric wafer active sensors (PWAS) which are "embedded." As used herein, the term "embedded" is intended to mean that the sensors are permanently attached directly to the surface of a thin wall structure (such as using a suitable adhesive) or are located inside the thin wall structure (such as by being located between layers of a laminate). The PWAS array will preferably perform structural health monitoring throughout the structure's life. Thus, unlike existing ultrasonic technology, the present invention provides an embedded, light weight, and inexpensive sensor arrangement, yielding a most likely candidate for an in-situ structural monitoring system. Further details regarding a preferred sensor for use in the system of the present invention can be found in copending application Ser. No. 10/072,644, filed Feb. 8, 2002, incorporated herein by reference.

Figure 2:
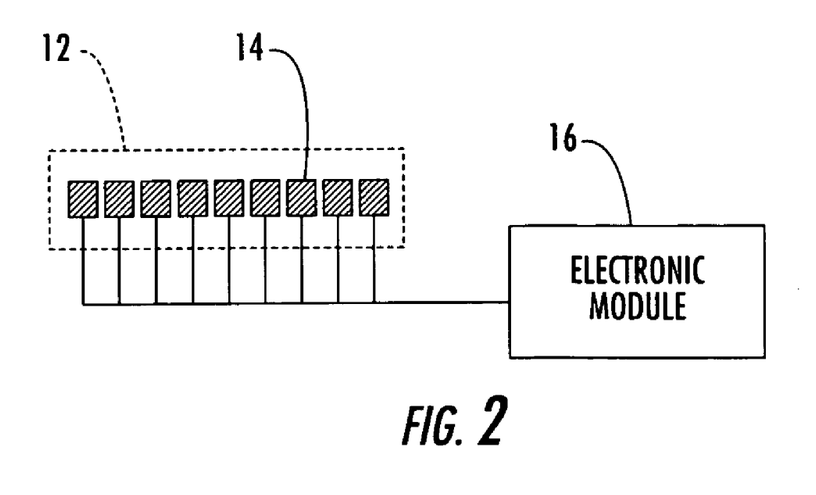
FIG. 2 is a diagrammatic representation of an apparatus constructed in accordance with the present invention.

As can be seen in FIG. 2, sensors 14 of array 12 are preferably placed on a straight line and are spaced by a distance equal to half of the wavelength of the guided wave propagating in the thin-wall structure. Sensors 14 communicate with an electronic module 16 for signal transmission/reception, processing and interpretation. Preferably, module 16 includes a tone-burst signal generator which creates a synthesized window-smoothed tone-burst signal with adjustable amplitude and repetition rate, a transmission beamformer (algorithm) at angle $\phi_0$, a reception beamformer (algorithm) at angle $\phi_0$, and a signal processor unit for signal deconvolution, time of flight (TOF), and range estimation.

Theoretical Aspects

In order to perform ultrasonic damage detection in thin-wall structures, the present invention utilizes a beamforming process analogous to that currently used in phased-array radar applications. The beamforming signal processing has been adapted to the specifics of guided elastic waves traveling in thin-wall structures. Advantageously, techniques of the present invention can be applied in thin-wall structures with either plane or curved surfaces. Because of this beamforming, the preferred embodiment can be referred as an "embedded ultrasonic structural radar" (EUSR).

The operation of the EUSR derives from two basic principles: (1) The principle of guided Lamb wave generation with piezoelectric wafer active sensors (PWAS) and (2) the principles of conventional phased-array radar adapted to PWAS-generated Lamb waves. The guided Lamb waves generated by the PWAS have the important property that they stay confined inside the walls of a thin-wall structure, and hence can travel over large distances. Additionally, the guided wave can also travel inside curved walls, which makes them ideal for applications in the ultrasonic inspection of aircraft, missiles, pressure vessel, oil tanks, pipelines, etc.

Lamb waves are dispersive and can exist in a number of modes. However, through smoothed tone-burst excitation and frequency tuning, it is possible to confine the excitation to a particular Lamb wave mode, of carrier frequency $F_c$, wave speed c, and wave length $\lambda = c/F_c$.

Figure 3A:
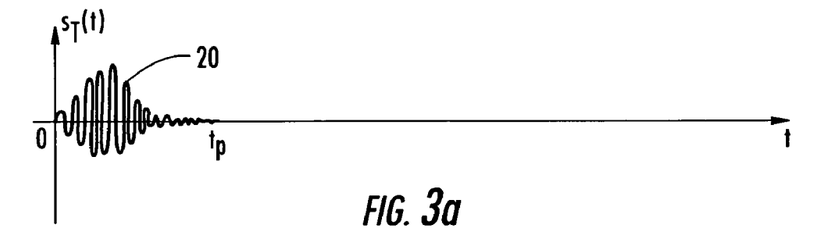
FIGS. 3a and 3b are respective plots showing a pulse and a resultant echo of an ultrasonic signal that can be produced using a piezoelectric sensor of the present invention.
Figure 3B:
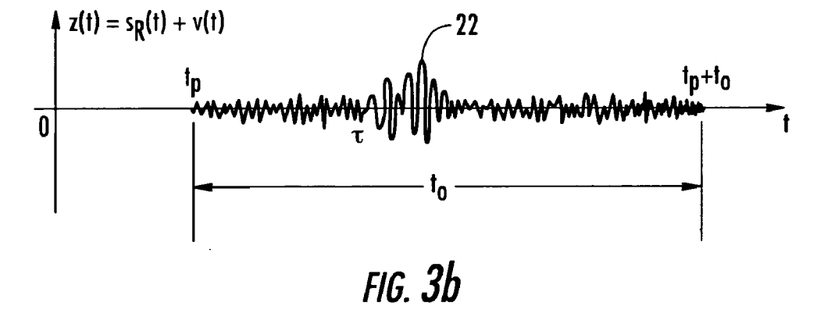

In this regard, FIGS. 3a and 3b illustrate the basis for the pulse-echo method. Specifically, FIG. 3a illustrates a transmitted smooth-windowed tone-burst signal 20 (of duration $t_p$). This signal, as would be generated by one PWAS, is of the form:

$$s_T(t) = s_0(t)\cos 2\pi F_c t, 0 < t < t_p \qquad (1)$$

Where $s_0(t)$ is a short-duration smoothing window that is applied to the carrier signal of frequency $F_c$ between 0 and $t_p$. FIG. 3b represents a received signal 22 to be a analyzed for the duration $t_0$, starting at $t_p$, in order to identify the time of flight (TOF) delay, $\tau$.

Excitation and reception of high-frequency Lamb waves was verified over a large frequency range (10 to 600 kHz). In typical embodiments, the preferred frequency will exist at a frequency of 100 kHz and above. For example, through these frequency tuning studies, a maximum wave response was found to exist around 300 kHz. Frequencies in the MHz range are contemplated in certain cases.

As noted above, the sensors 14 in the array 12 are preferably arranged as a uniform linear array, with each sensor acting as a pointwise omni-directional transmitter and receiver. As shown in more detail in FIG. 4, sensors 14 are spaced at a distance d, which is assumed much smaller than the distance r to a generic, far-distance point P. Since d<<r, the rays 24 joining the sensors 14 with the point P can be assimilated with a parallel fascicle of azimuth $\phi$. Generally, the number M of sensors in the array will fall in the range of three to twenty-one.

Figure 4:
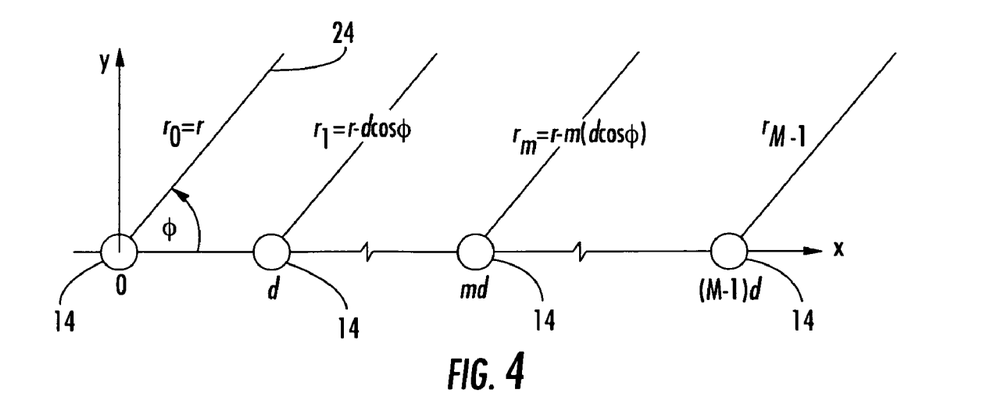
FIG. 4 is a diagrammatic representation of a uniform linear array of omni-directional sensors as may be utilized in accordance with the present invention.

Because of the array spacing, the distance between one sensor 14 and the generic point P will be different from the distance between another sensor 14 and P. For the m-th sensor, the distance will be shortened by $m(d\cos\phi)$. If all of the sensors 14 are fired simultaneously, the signal from the m-th PWAS will arrive at P quicker by $$\Delta_m(\phi) = m\frac{d}{c}\cos(\phi).$$

If the sensors are not fired simultaneously, but with some individual delays, $\delta_m$, m=0,1, ..., M−1, then the total signal received at point P will be:

$$s_P(t) = \frac{1}{r}\sum_{m=0}^{M-1} s_T\left(t - \frac{r}{c} + \Delta_m(\phi) - \delta_m\right) \qquad (2)$$

where 1/r represents the decrease in the wave amplitude due to omni-directional 2-D radiation, and r/c is the delay due to travel distance between the reference PWAS (m=0) and the point P.

Figure 5:
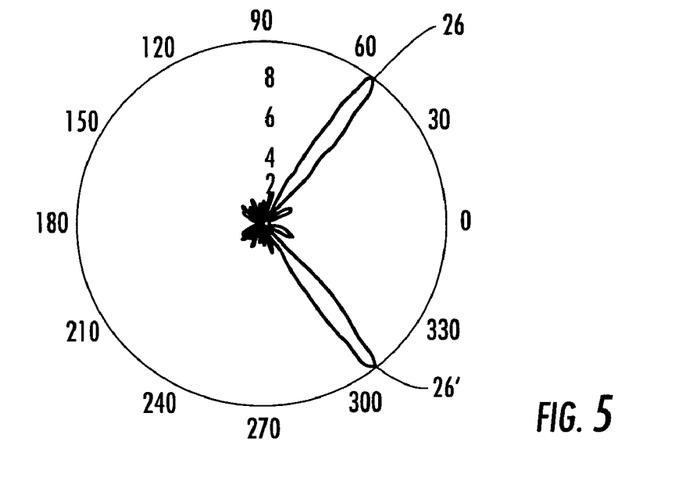
FIG. 5 is a graphical representation of a predicted beamforming pattern for a sensor array in accordance with an embodiment of the present invention.

Transmitter beamforming at angle $\phi_0$ with an array of M omni-directional sensors is based on the principles of constructive interference in the fascicle of parallel rays emanating from the array. The simplest way of achieving constructive interference is to have $\delta_m = m\Delta(\phi)$, such that Eq. 2 becomes:

$$s_P(t) = M \cdot \frac{1}{r} s_T\left(t - \frac{r}{c}\right) \tag{3}$$

i.e. an M times increase in the signal strength with respect to a simple sensor. This leads directly to the beamforming principle, i.e. if $$\delta_m = m\frac{d}{c}\cos(\phi_0),$$

and since $$\Delta_m(\phi) = m\frac{d}{c}\cos(\phi).$$

then constructive interference (beamforming) takes place when $\cos(\Phi) = \cos(\Phi_0)$, i.e. at angles $\phi = \phi_0$ and $\phi = -\phi_0$. Thus, the forming of a beam at angles $\phi_0$ and $-\phi_0$ is achieved through delays in the firing of the sensors in the array. For example, FIG. 5 shows beamforming patterns 26, 26' for $\phi_0 = 53°, -53°$.

The receiver beamforming principles are reciprocal to those of the transmitter beamformer. If the point P is an omni-directional source at azimuth $\phi_0$, then the signals received at the m-th sensor will arrive quicker by $$m\Delta(\phi) = m\frac{d}{c}\cos(\phi_0).$$

Hence, the signals received at all the sensors can by synchronized by delaying them by $$\delta_m(\phi_0) = m\frac{d}{c}\cos(\phi_0).$$

The phased-array pulse-echo method can by exemplified by assuming that a target exists at azimuth $\phi_0$ and distance R. The transmitter beamformer is sweeping the azimuth in increasing angles $\phi$ and receives an echo when $\phi = \phi_0$. The echo will be received on all sensors, but the signals will not be synchronized. To synchronize the sensors' signals, the delays $$\delta_m(\phi_0) = m\frac{d}{c}\cos(\phi_0)$$

are applied.

The synchronization process proceeds as follows, the signal sent by the transmitter beamformer is an M times boost of the original signal:

$$s_P(t) = \frac{M}{R} s_T\left(t - \frac{2R}{c}\right) \tag{4}$$

At the target, the signal is backscattered with a backscatter coefficient, A. Hence, the signal received at each sensor will be $$\left(\frac{A \cdot M}{R^2}\right) s_T\left(t - \frac{2R}{c} + \Delta_m(\phi)\right).$$

The receiver beamformer assembles the signals from all the sensors with the appropriate time delays:

$$s_R(t) = \frac{A \cdot M}{R^2} \sum_{m=0}^{M-1} s_T\left(t - \frac{2R}{c} + \Delta_m(\phi) - \delta_m\right) \tag{5}$$

Constructive interference between the received signals is achieved when $$\delta_m = m\frac{d}{c}\cos(\phi_0).$$

Thus, the assembled receive signal will be again boosted M times, with respect to the individual sensors:

$$s_R(t) = \frac{A \cdot M^2}{R^2} \sum_{m=0}^{M-1} s_T\left(t - \frac{2R}{c}\right) \tag{6}$$

The time delay between the receive signal, $s_R(t)$ and the transmit signal $s_T(t)$, is $$\tau = \frac{2R}{c} \tag{7}$$

Measurement of the time delay $\tau$ observed in $s_R(t)$ allows one to calculate the target range, $$R = \frac{c \cdot \tau}{2}.$$

As described, the present invention contemplates embedding piezoelectric wafer transducers on mechanical structures for potentially long periods of time. Thus, it is desirable to intermittently monitor the integrity of a transducer or transducer array. Accordingly, a self-diagnostic may be employed in which the reactive part of the transducer's impedance is measured over a relatively broad frequency range. Piezoelectric active sensors are predominately capacitive devices dominated by reactive impedance. Baseline impedance signatures can be used to identify defective active sensors. The appearance of sensor free-vibration resonance and the disappearance of structural resonances provide unambiguous features that indicate the degree of the transducer's integrity. Thus, through analysis of these changes, active sensor integrity self-diagnostics can be achieved by monitoring changes in the imaginary part of the electromechanical impedance spectrum and signaling when the sensor is no longer perfectly attached to the structure.

Practical Implementation

Figure 13:
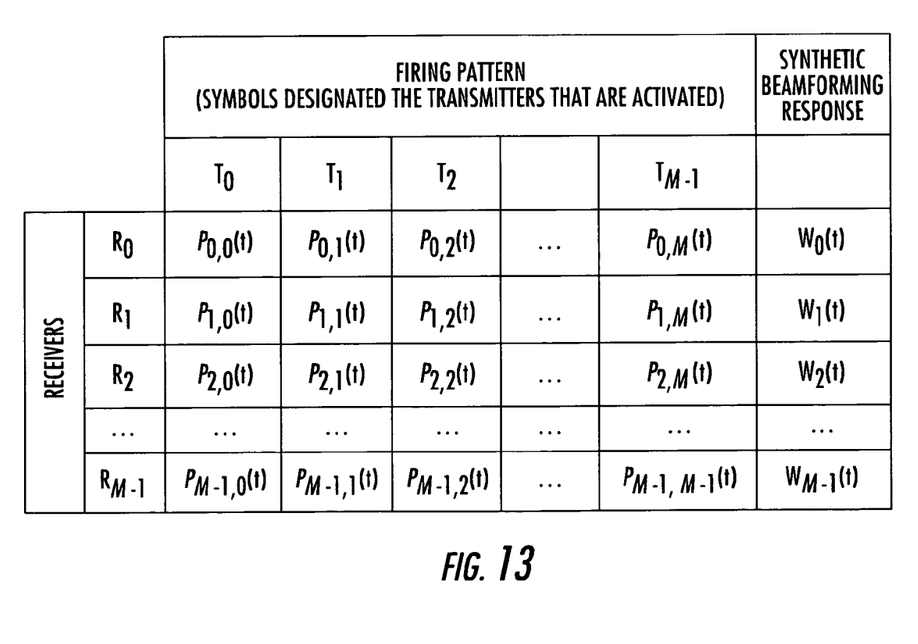
FIG. 13 is a table of signal primitives generated in a round-robin phase-array activation of the active-sensor array in accordance with an embodiment of the present invention.

In one presently preferred embodiment, the signal generation and collection may proceed as follows. In round-robin fashion, one active sensor at a time is activated as a transmitter. The reflected signals are received at all the sensors with the activated sensor acting in pulse-echo mode (i.e., as a transmitter and a receiver), and the other sensors acting as passive sensors. Thus an M×M matrix of signal primitives is generated (FIG. 13).

The signal primitives are assembled into synthetic mean-responses using a synthetic beamformer algorithm:

$$w_i(t) = \sum_{j=0}^{M-1} p_{ij}(t - \delta_j), \delta_j = j\Delta_0, \quad (8)$$

$$j = 0, 1, \ldots, M-1, \Delta_0 = \frac{d}{c}\cos\phi_0$$

Note that the delays, $\delta_j$, are selected in such a way as to steer the interrogation beam at a certain angle, $\phi_0$. The synthetic-beam sensor responses, $w_i(t)$, synthesized for a transmitter beam with angle $\phi_0$ are assembled by the receiver beamformer into the total received signal, $s_R(t)$, using the same delay as for the transmitter beamformer:

$$s_R(t) = \sum_{i=0}^{M-1} w_i(t - \delta_i) = \sum_{i=0}^{M-1} \sum_{j=1}^{M-1} p_{ij}(t - \delta_i - \delta_j) \quad (9)$$

However, this method presumes that the target angle $\phi_0$ is known in advance. In general applications, the target angle is not known, and needs to be determined. Hence, the received signal is written as a function of the parameter $\phi_0$:

$$s_R(t; \phi_0) = \sum_{i=0}^{M-1} \sum_{j=1}^{M-1} p_{ij}(t - \delta_i(\phi_0) - \delta_j(\phi_0)) \quad (10)$$

$$= \sum_{i=0}^{M-1} \sum_{j=1}^{M-1} p_{ij}(t - i \cdot \Delta_0(\phi_0) - j \cdot \Delta_0(\phi_0)) \text{ or}$$

$$s_R(t; \phi_0) = \sum_{i=0}^{M-1} \sum_{j=1}^{M-1} p_{ij}(t - (i+j) \cdot \Delta_0(\phi_0)) \quad (11)$$

Where $$\Delta_0(\phi_0) = \frac{d}{c}\cos\phi_0$$

is the array unit delay for the direction $\phi_0$. In practical implementation of the method, a spline interpolation approach has been used to implement the time shifts with accuracy at times that fall in between the fixed values of the sampled time.

A coarse estimate of the target direction is obtained in this case by using a virtual azimuth sweep technique. This azimuth sweep automatically increments the beam angle $\phi_0$ in Equation 8 by synthesizing the signal primitives with a starting angle of $\phi_0=0$ deg and then repeating the algorithm while incrementing $\phi_0$ by 1° for each calculation. The beam angle, $\phi_0$, is automatically modified until the maximum received energy is obtained:

$$\max E_R(\phi_0), \quad E_R(\phi_0) = \int_{t_p}^{t_p+t_0} |s_R(t, \phi_0)|^2 \, dt \quad (12)$$

After a coarse estimate of the target direction, $\phi_0$, is found, the actual round-trip time of flight, $\tau_{TOF}$, is calculated using an optimal estimator, e.g., the cross-correlation between the received and the transmitted signal:

$$y(\tau) = \int_{t_p}^{t_p+t_0} s_R(t) s_T(t - \tau) \, dt \quad (13)$$

Then, the estimated $\tau_{TOF}=2R/c$ is attained at the value of $\tau$ where $y(\tau)$ is maximum. Hence, the estimated target distance is $$R_{\exp} = \frac{c\tau_{TOF}}{2} \quad (14)$$

This algorithm works best for targets in the far field, for which the "parallel-rays" assumption holds.

For targets in the near and intermediate field, a more sophisticated self-focusing algorithm, that uses triangulation principles, is preferably used. This algorithm is an outgrowth of current passive-sensors target-location methodologies. The self-focusing algorithm modifies the delay times for each synthetic-beam response, $w_i(t)$, such that it maximizes the total response, by finding the focal point of individual responses, i.e., the common location of the defect that generated the echoes recorded at each sensor. For very close range targets, synthetic aperture focusing techniques (SAFT) can be utilized.

Two versions of the apparatus are contemplated, a "lightweight" version and a "heavy duty" version. The lightweight inexpensive version preferably uses single-channel switching to collect the individual signal primitives from all the sensors, for all firing patterns, one sensor at a time. The collected signal primitives may be stored in flash memory and processed in a batch after the data collection phase has finished.

The principle of operation of this lightweight version relies on the assumption of linear superposition and the existence of steady structural behavior during data collection. Using appropriate time-shifting, the data components corresponding to each sensor and firing pattern are assembled into a total response signal using a synthetic-aperture beamforming/focusing algorithm. Because this version typically uses only one channel for signal transmission and reception, its electronics are relatively simple and light. The synthetic aperture beamforming/focusing algorithm may be performed with a programmable DSP (digital signal processing) chip in quasi-real time. The lightweight version is ideally suited for structural health monitoring applications, which do not require fast real-time structural inspection capabilities.

The heavy-duty version is generally faster, more sophisticated, but heavier. This version may be employed when the linear superposition principle cannot be successfully applied. This could happen when detrimental signal to noise ratio (SNR) exists, or when the material system has nonlinear behavior. This version can also be used when fast real-time inspection is required.

Preferably, the heavy duty version utilizes real-time transmission and reception beamforming, with all the active sensors in the array being simultaneously fired. To achieve this, ample electronics that can handle the firing of all the sensors in parallel with the prescribed time spacing are utilized. The electronics and signal processing may be similar to that currently used in real-time sensor-array ultrasonic medical imaging.

Experimental Results

Figure 6A:
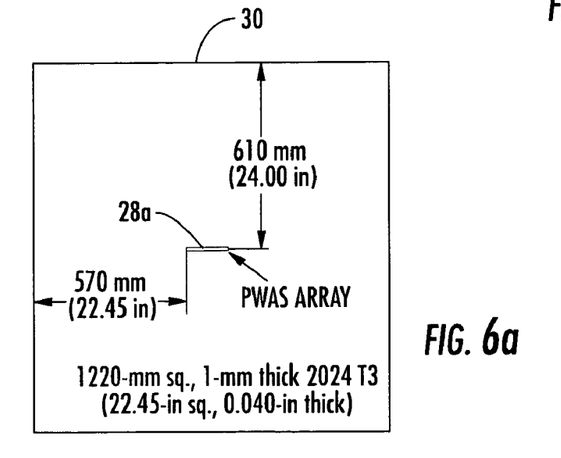
FIGS. 6a, 6b, 7a and 7b are diagrammatic representations of a proof-of-concept experiment as will be described.
Figure 7A:
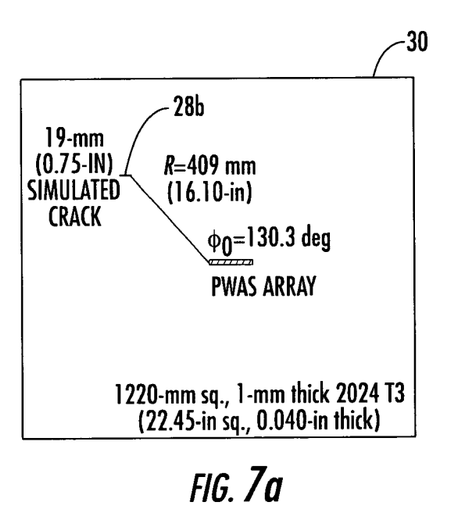

The concept described above has been reduced to practice in proof-of-concept experiments. In these experiments, small simulated-cracks were detected at broadside and off-angle locations on a thin sheet specimen. As shown in FIGS. 6a and 7a; the simulated cracks 28a and 28b were 19 mm (¾-in) long, 0.127 mm (0.005-in) wide. The specimen was a 1220-mm (4-ft) square panel 30 of 1-mm (0.040-in) thick 2024-T3 Al-clad aircraft grade sheet metal stock. The simulated cracks were placed: (a) broadside at R=305 mm from the PWAS array; and (b) offside at R=453 mm, $\phi_0$=130.3 deg. The signal processing algorithm allowed the detection of the simulated cracks and their positions with good accuracy.

Figure 8:
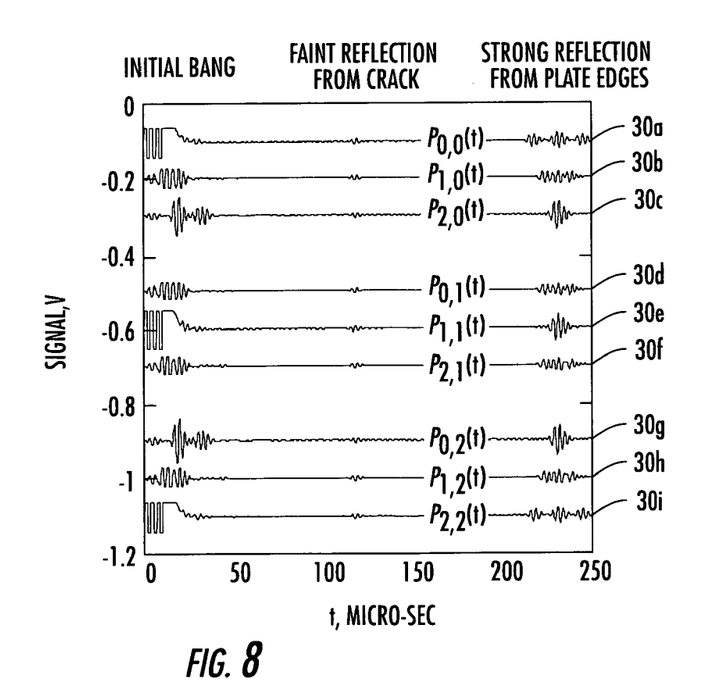
FIG. 8 is a plot of multiple primitives obtained in a broadside detection experiment.

FIG. 8 shows the nine signal primitives (indicated by the reference numbers 30a–i), $p_{ij}$(t), i, j=0, 1, 2 (M=3), obtained with a 3-sensor array during a broadside detection experiment. Present in each signal are the initial bang, a strong reflection from the plate edges, and a faint reflection from the crack. The top set of three signals correspond to excitation from the first sensor (j=0) and reception on all the three sensors (i=0, 1, 2). It will be appreciated that the initial bang applied by the first sensor is also received as a direct tremor at the other two array sensors after very short times. As expected, the sensor next to the excited sensor receives the tremor first, while the sensor further apart from the first sensor receives the tremor after a slight delay.

In the second group of three signals of FIG. 8, the center sensor was excited; hence the initial bang is noticed on that signal. The tremors of the initial bang received at the adjacent sensors appear identical, since these sensors are placed symmetrically with respect to the excited sensor. The last group of three signals corresponds to the third sensor being excited. This group is a mirror image of the first group. It can be appreciated that the faint crack-reflection signals are offset in time by small delays.

Figure 9:
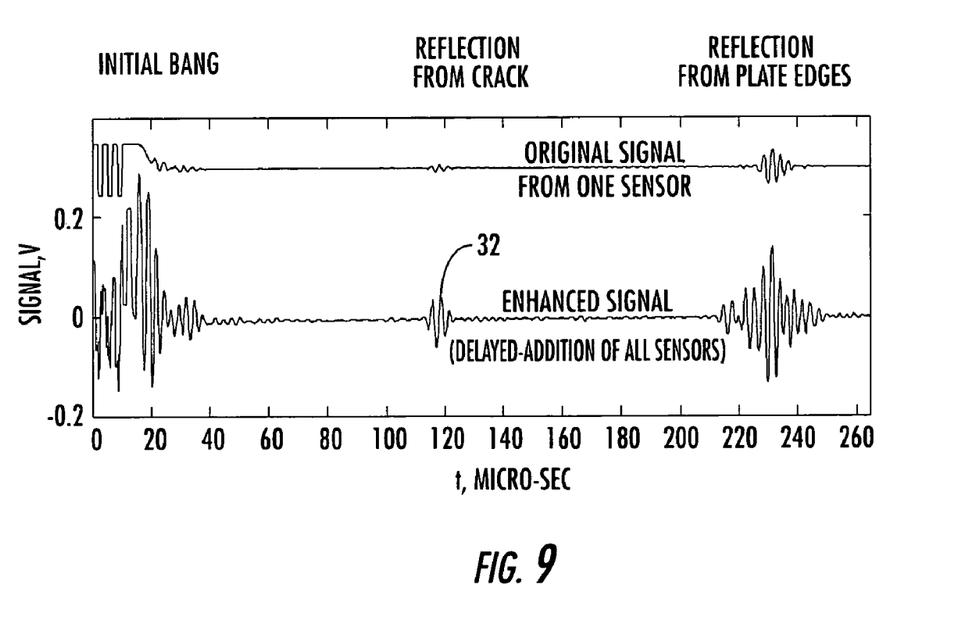
FIG. 9 illustrates signal enhancement using the proposed phased-array method in accordance with an embodiment of the present invention.

In all the nine signals, a reflection echo due to the simulated crack is present. However, this echo is very faint, and has a very poor signal to noise ratio (SNR) in this case. However, FIG. 9 presents an enhanced signal (indicated by the reference number 32), $s_R$(t), obtained by the delayed-addition of all the sensor signals as described herein. The SNR of the enhanced signal is better than the original signal. In this enhanced signal, the arrival time of the crack echo can be easily identified as $\tau_{TOF}$=112.4 micro-sec. Using group velocity $c_g$=5.440 mm/micro-sec yields the range of the crack as $R_{exp}$=305.7 mm. The exact value of the range is R=305 mm. The range estimation error is a mere 0.2%.

Figure 6B:
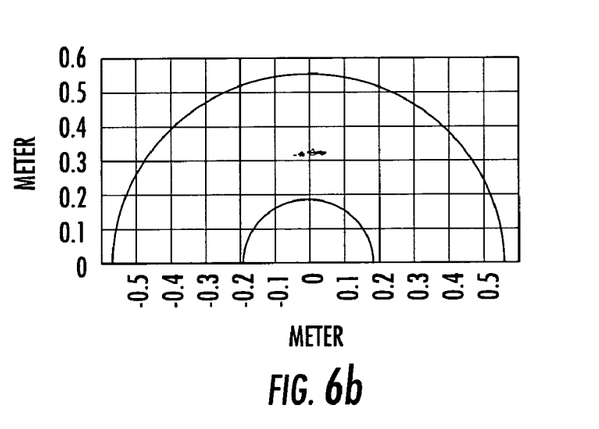
Figure 10:
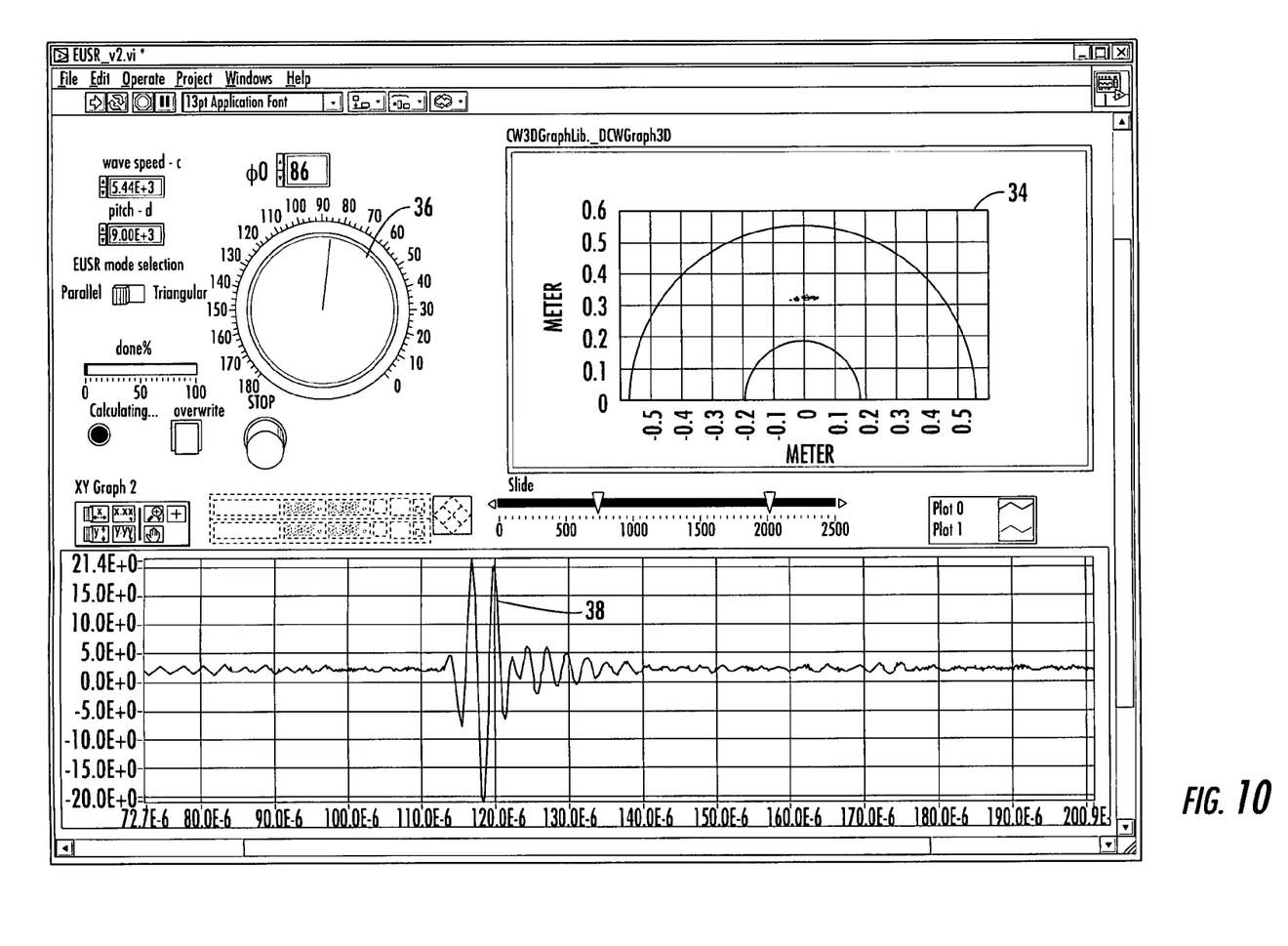
FIG. 10 is an illustration of an exemplary graphical user interface (GUI) during the broadside experiment of FIGS. 6a and 6b.

The crack imaging in the plate using the EUSR method for the broadside experiment is shown in FIG. 6b. FIG. 10 presents the front panel of the embedded ultrasonic structural radar graphical user interface (EUSR-GUI) constructed for this application. The angle sweep is performed automatically to produce the structure/defect imaging picture 34 on the right. Manual sweep of the beam angle can be also performed with the turn knob 36; the signal 38 reconstructed at a particular beam angle (here, $\phi_0$=86 deg) is shown in the lower picture of FIG. 10.

Figure 11:
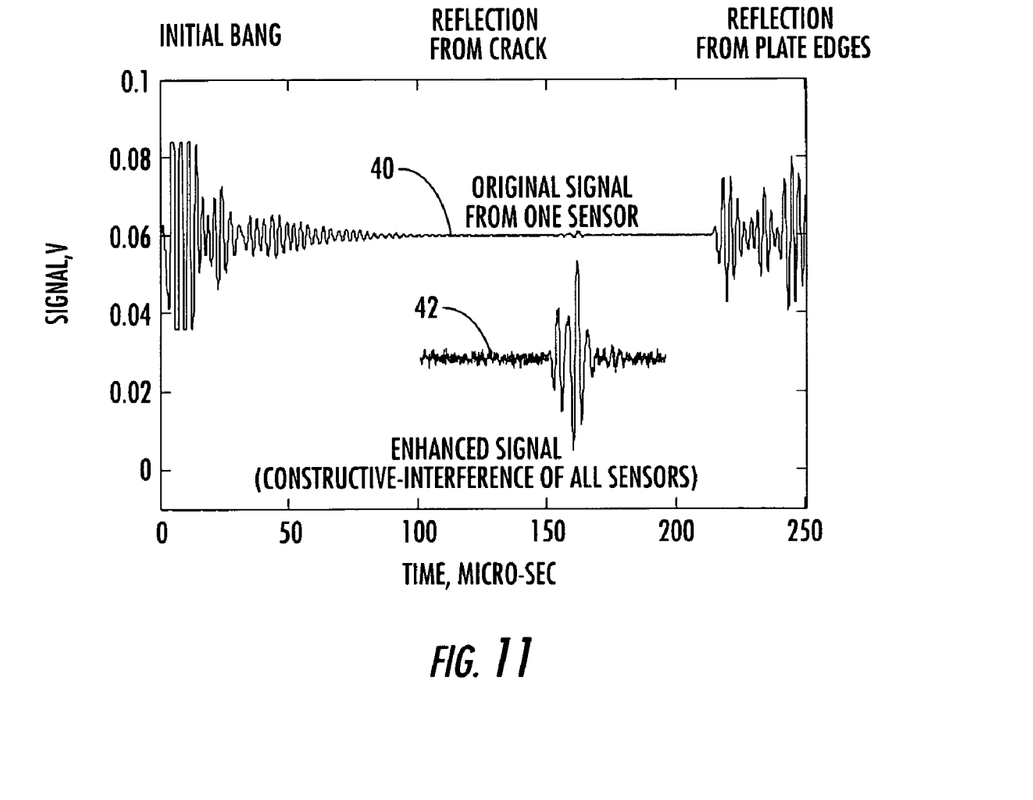
FIG. 11 illustrates signal enhancement using the proposed phased-array method in accordance with an embodiment of the present invention.

FIG. 11 presents the results for the offside crack experiment. Because of the inclination of the crack, the backscatter reflections from the crack were much weaker than in the broadside experiment. Hence, all the signals from the full 9-sensor array had to be used. The original signal from one of the nine sensors is presented on the top line 40 of FIG. 11. The enhanced signal, $s_R$(t), is presented on the line 42. The enhanced signal was obtained by the constructive interference of all the original sensor signals, as described herein. For display purposes, the signals were shifted by a DC bias.

The original sensor signal 40 presented in FIG. 11 shows a very faint tremor at approximately 151 micro-sec representing the backscatter reflection from the crack. This signal is very faint because the crack is positioned offside, and the main beam of ultrasound interrogation is reflected away from the sensor array. Hence, the SNR of the individual sensor signal is very poor. Obviously, the original sensor signals cannot be used for crack detection. However, the SNR of the enhanced signal 42 is many times better. The enhanced signal can be used with ease for crack detection. In this enhanced signal, the arrival time of the crack echo is identified as $\tau_{TOF}$=151 micro-sec. Using group velocity cg=5.440 mm/micro-sec yields the range of the crack as $R_{exp}$=411 mm. The exact value (FIG. 7a) is R=409 mm. The range estimation error is 0.4%.

Figure 7B:
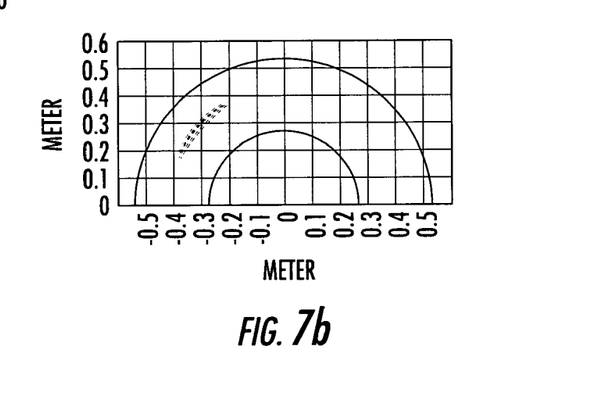
Figure 12:
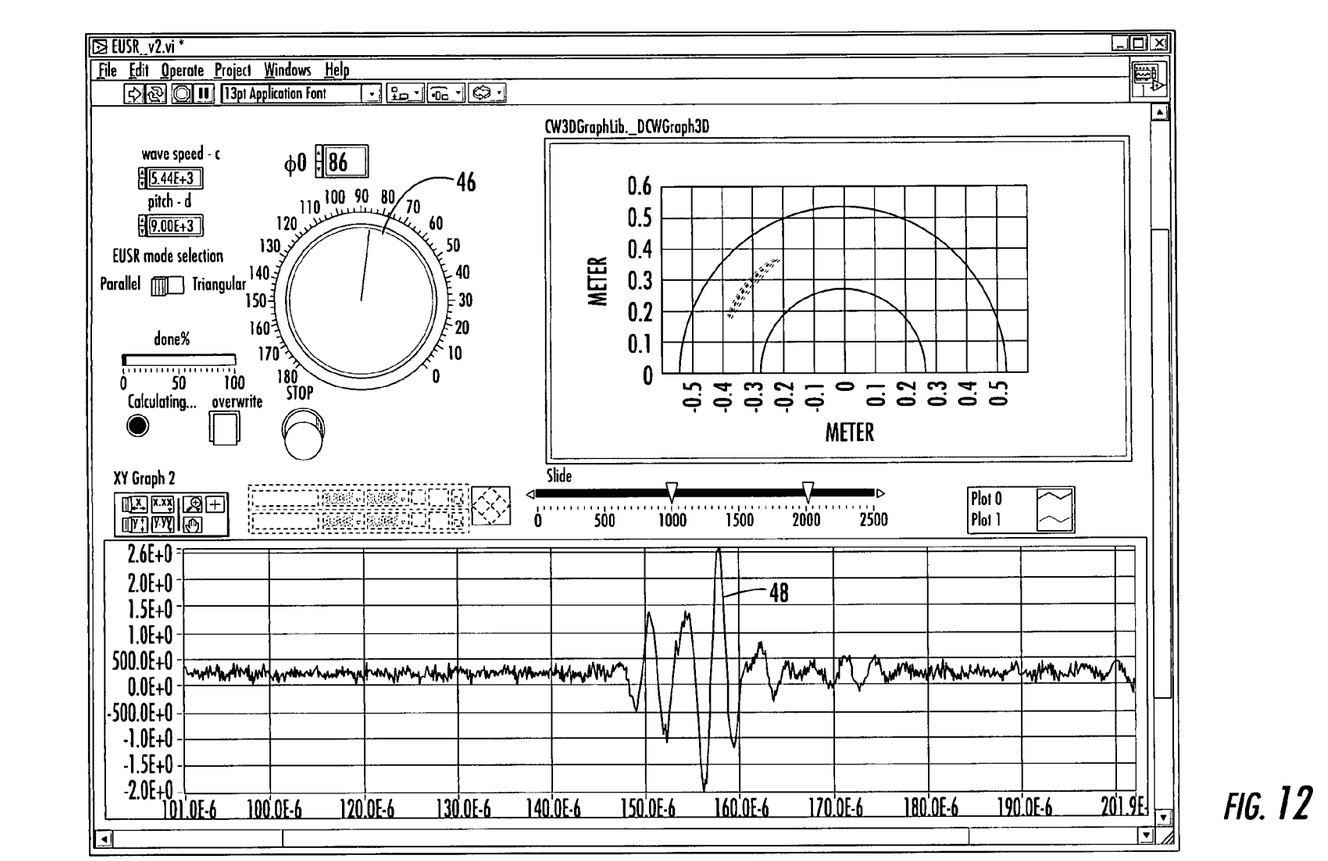
FIG. 12 is an illustration of the exemplary GUI during the off-angle experiment of FIGS. 7a and 7b.

The crack imaging in the plate using the EUSR method is shown in FIG. 7b. FIG. 12 presents the front panel of the EUSR-GUI displaying the offside signals. The angle sweep is performed automatically to produce the structure/defect imaging picture 44 on the right. Manual sweep of the beam angle can be also performed with the turn knob 46; the signal 48 reconstructed at a particular beam angle (here, $\phi_0$=136 deg) is shown in the lower picture of FIG. 12.

It can thus be seen that the present invention provide a structural health monitoring system in furtherance of the noted objects. While one or more preferred embodiments of the invention have been described above, it should be understood that any and all equivalent realizations of the present invention are included within the scope and spirit thereof. The embodiments depicted are presented by example only and are not intended as limitations upon the present invention. Thus, it should be understood by those of ordinary skill in the art that the present invention is not limited to these embodiments since modifications can be made. Therefore, it is contemplated that any and all such embodiments are included in the present invention as may fall within the literal or equivalent scope of the appended claims.

What is claimed is:

1. A system operative to detect a damage feature in a thin wall structure, said system comprising:
   a plurality of piezoelectric sensors embedded on said structure in a predetermined pattern;
   a generator operative to impress a pulse having a predetermined carrier frequency upon at least one of said sensors to produce guided ultrasonic waves that travel along said thin wall structure;

a signal processor operative to process received signals at said sensors resulting from an echo from said damage feature;

said processor implementing a synthetic beamforming methodology for determining an angular position of said damage feature spaced apart from said plurality of sensors along a plane of said thin wall structure; and said processor further calculating a distance to said damage feature.

2. A system as set forth in claim 1, wherein said plurality of sensors are linearly arranged.

3. A system as set forth in claim 2, wherein said sensors are separated by a spacing equal to approximately one-half a signal wavelength at said predetermined carrier frequency.

4. A system as set forth in claim 3, wherein said predetermined carrier frequency is at least 100 KHz.

5. A system as set forth in claim 4, wherein said predetermined carrier frequency is at least approximately 300 kHz.

6. A system as set forth in claim 2, wherein said plurality of sensors includes at least three sensors.

7. A system as set forth in claim 6, wherein said plurality of sensors includes no more than twenty-one sensors.

8. A system as set forth in claim 2, wherein said generator impresses said pulse on only one of said sensors per reading.

9. A system as set forth in claim 8, wherein said generator is operative to impress successive signals on respective sensors in round-robin fashion.

10. A system as set forth in claim 9, wherein a set of received signals for all sensors acting as a receiver for each of said sensors acting as a transmitter in round-robin fashion are collected so as to produce an enhanced signal.

11. A system as set forth in claim 10, wherein said angular position of said damage feature is determined via an energy calculation assuming a plurality of angles throughout a selected angular range.

12. A system as set forth in claim 10, wherein said enhanced signal is produced in subsequent processing based on a set of primitive signals received at each of said sensors.

13. A system as set forth in claim 10, wherein said synthetic beamforming methodology operates by applying time delays corresponding to selected angles to a set of primitive signals received at each of said sensors.

14. A system as set forth in claim 1, wherein a set of received signals for all sensors acting as a receiver for each of said sensors acting as a transmitter in round-robin fashion are collected so as to determine said angular position of said damage feature.

15. A system as set forth in claim 1, wherein said processor is operative to time shift and superimpose signals received at respective sensors to create an enhanced signal.

16. A system as set forth in claim 1, wherein said sensors respectively comprise piezoelectric wafer active sensors.

17. A system as set forth in claim 16, wherein said sensors are adhered to a surface of said thin wall structure.

18. A system operative to detect a damage feature in a thin wall structure, said system comprising:

a plurality of piezoelectric sensors embedded on said structure in a linear pattern;

a generator operative to impress a pulse having a predetermined carrier frequency upon said sensors so as to produce guided ultrasonic waves that travel along said thin wall structure at a predetermined azimuth;

a signal processor operative to process received signals at said sensors resulting from an echo from said damage feature, said damage feature being spaced apart from said sensors along a plane of said thin wall structure; and said processor calculating a distance to said damage feature.

19. A system as set forth in claim 18, wherein said generator is operative to impress said pulse on respective of said sensors with a predetermined time delay so as to produce constructive interference at said predetermined azimuth.

20. A system as set forth in claim 19, wherein said sensors are separated by a spacing equal to approximately one-half a signal wavelength at said predetermined carrier frequency.

21. A system as set forth in claim 20, wherein said predetermined carrier frequency is at least 100 KHz.

22. A system as set forth in claim 21, wherein said predetermined carrier frequency of approximately 300 kHz.

23. A system as set forth in claim 18, wherein said plurality of sensors includes at least three sensors.

24. A system as set forth in claim 18, wherein said plurality of sensors includes no more than twenty-one sensors.

25. A system as set forth in claim 18, wherein said sensors respectively comprise piezoelectric wafer active sensors.

26. A system as set forth in claim 25, wherein said sensors are permanently adhered to a surface of said thin wall structure.

27. A system as set forth in claim 18, wherein said generator is operative to sweep said azimuth over a predetermined angular range.

* * * * *